US008923586B1

(12) United States Patent
Amir

(10) Patent No.: US 8,923,586 B1
(45) Date of Patent: Dec. 30, 2014

(54) SYSTEM AND METHOD FOR MOLECULAR BREAST IMAGING

(71) Applicant: GE Medical Systems Israel Ltd, Tirat Hacarmel (IL)

(72) Inventor: Ormit Amir, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 20 days.

(21) Appl. No.: 13/951,852

(22) Filed: Jul. 26, 2013

(51) Int. Cl.
*G06K 9/00* (2006.01)
*A61B 6/00* (2006.01)

(52) U.S. Cl.
CPC ............ *A61B 6/4258* (2013.01); *A61B 6/4057* (2013.01)
USPC ....................................................... 382/128

(58) Field of Classification Search
CPC .................. G06T 7/0012; G06T 2207/30004; G06F 19/321
USPC ........................................................ 382/128
See application file for complete search history.

(56) References Cited

U.S. PATENT DOCUMENTS

| 6,310,477 | B1 | 10/2001 | Schneider |
| 7,872,221 | B2 | 1/2011 | Blevis et al. |
| 2013/0216113 | A1* | 8/2013 | O'Connor ..................... 382/128 |

* cited by examiner

*Primary Examiner* — Jurie Yun
(74) *Attorney, Agent, or Firm* — Dean D. Small; The Small Patent Law Group

(57) ABSTRACT

A method for generating molecular breast imaging (MBI) images includes generating at least one energy spectrum using an emission dataset acquired by imaging a patient, identifying a tail energy region and a peak energy region in the energy spectrum, determining a quantity of counts in the tail energy region and the peak energy region, generating an energy window for the energy spectrum based on the counts in the tail energy region and the peak energy region, and assigning a pixel intensity value to at least one image pixel based on a plurality of counts in the energy window.

20 Claims, 5 Drawing Sheets

SYSTEM AND METHOD FOR MOLECULAR BREAST IMAGING

BACKGROUND OF THE INVENTION

The subject matter disclosed herein relates generally to systems and methods for diagnostic medical imaging, and more particularly to Molecular Breast Imaging (MBI) systems.

Molecular Breast Imaging (MBI) is used to image breasts to detect, for example, tumors, lesions, and/or cancer. In operation, a patient is positioned within the MBI system such that the patient's breast is positioned between a pair of detectors. A plurality of two-dimensional (2D) images of the patient's breast is then acquired. More specifically, the detectors include a plurality of pixels that generate counts that are proportional to the energy spectrum of the radiopharmaceutical radiating from the patient.

In operation, the patient is injected with a radiopharmaceutical such as, for example, Technetium-99 (Tc99). As the radiopharmaceutical decays, the emitted gamma rays have a predefined energy spectrum that is typically unique for the radiopharmaceutical being utilized. For example, Tc99 has an energy spectrum having a peak energy of approximately 140 keV. The gamma rays are then detected by the detectors as counts which are subsequently used to generate an image of the patient. To identify the counts, the detectors utilize a predefined acceptance window such that gamma rays within a predetermined energy range of the radiopharmaceutical being imaged are defined as counts.

However, when the detectors are fabricated using a Cadmium Zinc Telluride, (CZT) material, the energy spectrum of the gamma rays includes a tail, e.g. additional information that is acquired outside of the energy window. For at least one known CZT detector, the total counts within the predefined acceptance window may therefore be composed of only approximately 60% of the energy spectrum of the Tc99. Accordingly, for CZT detectors, the conventional energy window may not be appropriately sized to include all the useful information or counts in the energy spectrum. As a result, because the count rate for each pixel in the detector is utilized to determine an intensity value for each pixel in the final image, various features of interest in the generated image may be difficult to distinguish from background tissue in the image.

BRIEF DESCRIPTION OF THE INVENTION

In accordance with various embodiments, a method for generating molecular breast imaging (MBI) images is provided. The method includes generating at least one energy spectrum using an emission dataset acquired by imaging a patient, identifying a tail energy region and a peak energy region in the energy spectrum, determining a quantity of counts in the tail energy region and the peak energy region, generating an energy window for the energy spectrum based on the counts in the tail energy region and the peak energy region, and assigning a pixel intensity value to at least one image pixel based on a plurality of counts in the energy window.

In another embodiment, a molecular breast imaging (MBI) system is provided. The MBI system includes at least one detector having a plurality of detector elements and a processing unit coupled to the detector. The processing unit is configured to generate at least one energy spectrum using an emission dataset acquired by imaging a patient, identify a tail energy region and a peak energy region in the energy spectrum, determine a quantity of counts in the tail energy region and the peak energy region, generate an energy window for the energy spectrum based on the counts in the tail energy region and the peak energy region, and assign a pixel intensity value to at least one image pixel based on a plurality of counts in the energy window.

In a further embodiment, a non-transitory computer readable medium is provided. The non-transitory computer readable medium is encoded with a program to instruct a processing unit to generate at least one energy spectrum using an emission dataset acquired by imaging a patient, identify a tail energy region and a peak energy region in the energy spectrum, determine a quantity of counts in the tail energy region and the peak energy region, generate an energy window for the energy spectrum based on the counts in the tail energy region and the peak energy region, and assign a pixel intensity value to at least one image pixel based on a plurality of counts in the energy window.

DETAILED DESCRIPTION OF THE INVENTION

Figure 1:
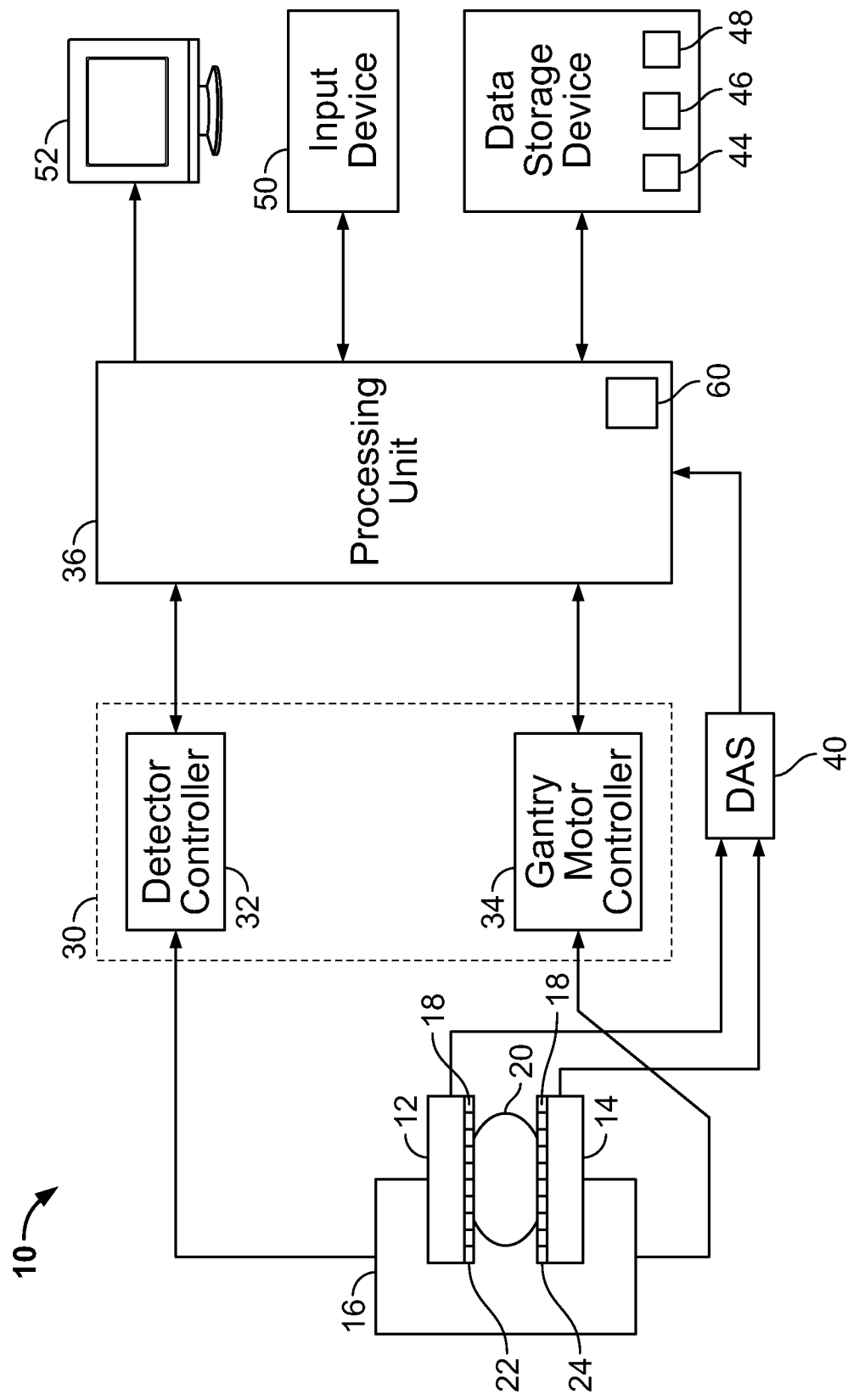
FIG. 1 a block diagram of an exemplary nuclear medicine imaging system embodied as a Molecular Breast Imaging (MBI) system constructed in accordance with various embodiments.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide a method for determining a size of a window utilized to identify counts and utilizing the identified counts to generate an image of the patient using a Nuclear Medicine (NM) imaging system. For example, various embodiments provide a Molecular Breast Imaging (MBI) system and a method to acquire temporal emission data of a patient's breast. Temporal as used herein means that the emission data is time stamped such that a location of an event detected by the detectors may be associated with a time when the event was detected by the detectors. The temporal emission data may be acquired in real-time while the MBI system is performing a dynamic scan of the breast. Optionally, the temporal emission data may be acquired after the breast is scanned. In various embodiments, the temporal emission data is stored as list mode data. The list mode data may then be utilized to generate a plurality of energy spectrums, wherein each energy spectrum is generated using emission data acquired from one or more detector elements in the detectors. The energy spectrums are then analyzed to generate a ratio of the counts recorded proximate to a peak region in the energy spectrum and the counts recorded in a tail region of the energy spectrum. The size of an energy window is then modified based on the ratio.

The energy window is utilized to select a plurality of counts utilized to generate an image. The energy window therefore has an energy range to identify or select counts that fall within the predetermined energy range. For example, a width of the energy window may be increased, such that more counts are included, when the energy spectrum is acquired from detector elements located away from the chest wall where less scatter is expected. Moreover, a width of the energy window may be decreased when the energy spectrum is acquired from detector elements located proximate to the chest wall where more scatter is expected. After adjusting a width of the energy window, the counts included within the energy window are used to define pixel intensity values in a final image. Adjusting a width of the energy window therefore improves the overall image quality by reducing scatter related artifacts that may occur near the chest wall and increasing the amount of emission data utilized to generate the pixel intensity values for image pixels located away from the chest wall. Accordingly, automatically adjusting the width of energy window results in higher detector sensitivity and therefore improves detectability of, for example, lesions. In CZT imaging systems, a wider energy window improves the sensitivity but may also enable more scatter data to be collected which may degrade the lesion detectability. Accordingly, the various embodiments described herein enable optimal lesion detectability by automatically choosing the optimal energy window for the various regions in the image. Improved lesion detectability therefore increases the sensitivity and specificity of the system.

In various embodiments, the methods described herein may be implemented using, for example, Single-Photon Emission Computed Tomography (SPECT) systems, Positron Emission Tomography (PET) systems, and Molecular Breast Imaging (MBI) systems, among other nuclear medicine detector systems. Accordingly, while the illustrated embodiments are described with respect to a MBI system being utilized to image a breast, the various embodiments described herein may be implemented using any nuclear medicine system configured to image any portion of the patient. Additionally, the MBI system may be a standalone imaging system or form part of a multi-modality imaging system.

In various embodiments, the methods described herein may be implemented using an exemplary MBI system 10 shown in FIG. 1. The MBI system 10 includes imaging detectors 12 and 14 mounted on or to a gantry 16. Each of the detectors 12 and 14 include an array of CZT detector elements 18 that generally capture emission data that may be defined by the x and y location of the detector element in the array. Moreover, in various embodiments, the emission data captured by the detector 12 is obtained from a view that is approximately 180 degrees away from the emission data captured by the detector 14. Further, in other exemplary embodiments, at least one of the detectors 12 and 14 may change orientation relative to the stationary or movable gantry 16. The detectors 12 and 14 may be registered such that features appearing at a given location in one detector may be correctly located and the data correlated in the other detector. Accordingly, in various embodiments common features in the two images acquired by the imaging detectors 12 and 14 may be combined. Moreover the methods described herein are applicable to imaging systems using only a single detector i.e. detector 12, for example.

Each of the detectors 12 and 14 has a radiation detection face that is formed by the detector arrays 18, and is directed towards a structure of interest, for example, a breast 20. As described above, although the illustrated embodiment is described with respect to the breast 20, the methods described herein may be utilized to image any portion of the patient. A pair of collimators 22 and 24 may be provided in combination or connection with the detectors 12 and 14, respectively. In various embodiments, the radiation detection faces of the detectors 12 and 14 are covered by the collimators 22 and 24. In some embodiments, the collimators 22 and 24 are registered parallel holes collimators coupled to the detection faces of the detectors 12 and 14.

For example, the detectors 12 and 14 may include collimators 22 and 24, respectively, provided directly on the surface of the detectors 12 and 14 and illustrated as parallel hole collimators. The detectors 12 and 14 are also capable of being rotated to some angle to provide various images of the breast 20 while remaining substantially parallel to each other. Additionally, the distance between the two detectors 12 and 14 may be changed to accommodate breasts with different sizes and to immobilize the breast for the duration of data acquisition, which may include applying light pressure to the breast. The distance between near faces of the two collimators 22 and 24 is registered automatically or manually. Although illustrated as a parallel hole collimators 22 and 24, different types of collimators as known in the art may be used, such as pinhole, fan-beam, cone-beam, and diverging type collimators. An actual field of view (FOV) of each of the detectors 12 and 14 may be directly proportional to the size and shape of the respective imaging detector, or may be changed using collimation. In various embodiments, the detectors 12 and 14 are formed of cadmium zinc telluride (CZT) detector elements 18 as described above. Optionally, the detectors 12 and 14 may be any suitable two-dimensional pixelated detector.

The MBI system 10 also includes a motion controller unit 30 to control the movement and positioning of the gantry 16 and/or the detectors 12 and 14 with respect to each other to position the breast 20 within the FOVs of the imaging detectors 12 and 14 prior to acquiring an image of the breast 20. The controller unit 30 includes a detector controller 32 and a gantry motor controller 34 that may be automatically commanded by a processing unit 36, manually controlled by an operator, or a combination thereof. The gantry motor controller 34 and the detector controller 32 may move the detectors 12 and 14 with respect to the breast 20 individually, in segments or simultaneously in a fixed relationship to one another. Alternatively, one or more collimators 22 and 24 may be moved relative to the detectors 12 and 14. The distance between the detectors 12 and 14 may be registered by the controller unit 30 and used by the processing unit 36 during data processing. In some embodiments, motion is manually detected by the operator and the controller unit 30 is replaced with scales or encoders for measuring the distance between the detectors 12 and 14, the detector orientation, and/or any immobilization force exerted by at least one detector 12 and/or 14 on the breast 20.

During operation, the breast 20 is positioned between the detectors 12 and 14 and at least one of the detectors 12 and/or 14 is translated to immobilize the breast 20 between the detectors 12 and 14. The detectors 12 and 14 are then used to acquire temporal image data of the breast 20, which may include one or more lesions, for example a breast cancer tumor, within the breast 20. The detectors 12 and 14 and the gantry 16 generally remain stationary after being initially positioned, and the temporal emission data is acquired. The temporal emission data may then be combined into a composite image that includes a plurality of two-dimensional (2D) images 46, wherein each 2D image 46 is acquired at a different point in time during the scan.

The MBI system 10 also includes a Data Acquisition System (DAS) 40 that receives analog and/or digital electrical signal data produced by the detectors 12 and 14 and decodes the data for subsequent processing in the processing unit 36. A data storage device 42 may be provided to store data from the DAS 40 or other types of data. For example, the data storage device 42 may store emission data 44 acquired from the detectors 12 and 14 during a scan of the breast 20. In various embodiments, the emission data 44 may be utilized generate a plurality of 2D images or frames 46 of the breast 20. Optionally, the emission data 44 may be stored as list mode data 48 of the breast 20 acquired during a previous scan, e.g. event-by-event data acquisition. An input device 50 (e.g., user console with keyboard, mouse, etc.) also may be provided to receive user inputs and a display 52 may be provided to display images.

In various embodiments, the MBI system 10 also includes an energy window generating module 60 that is configured to implement various methods described herein. The module 60 may be implemented as a piece of hardware that is installed in, for example, the processing unit 36. Optionally, the module 60 may be implemented as a set of instructions that are installed on the processing unit 36. The set of instructions may be stand alone programs, may be incorporated as subroutines in an operating system installed on the processing unit 36, may be functions in an installed software package on the processing unit 36, and the like. It should be understood that the various embodiments are not limited to the arrangements and instrumentality shown in the drawings.

The set of instructions may include various commands that instruct the module 60 and/or the processing unit 36 as a processing machine to perform specific operations such as the methods and processes of the various embodiments described herein. The set of instructions may be in the form of a non-transitory computer readable medium. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
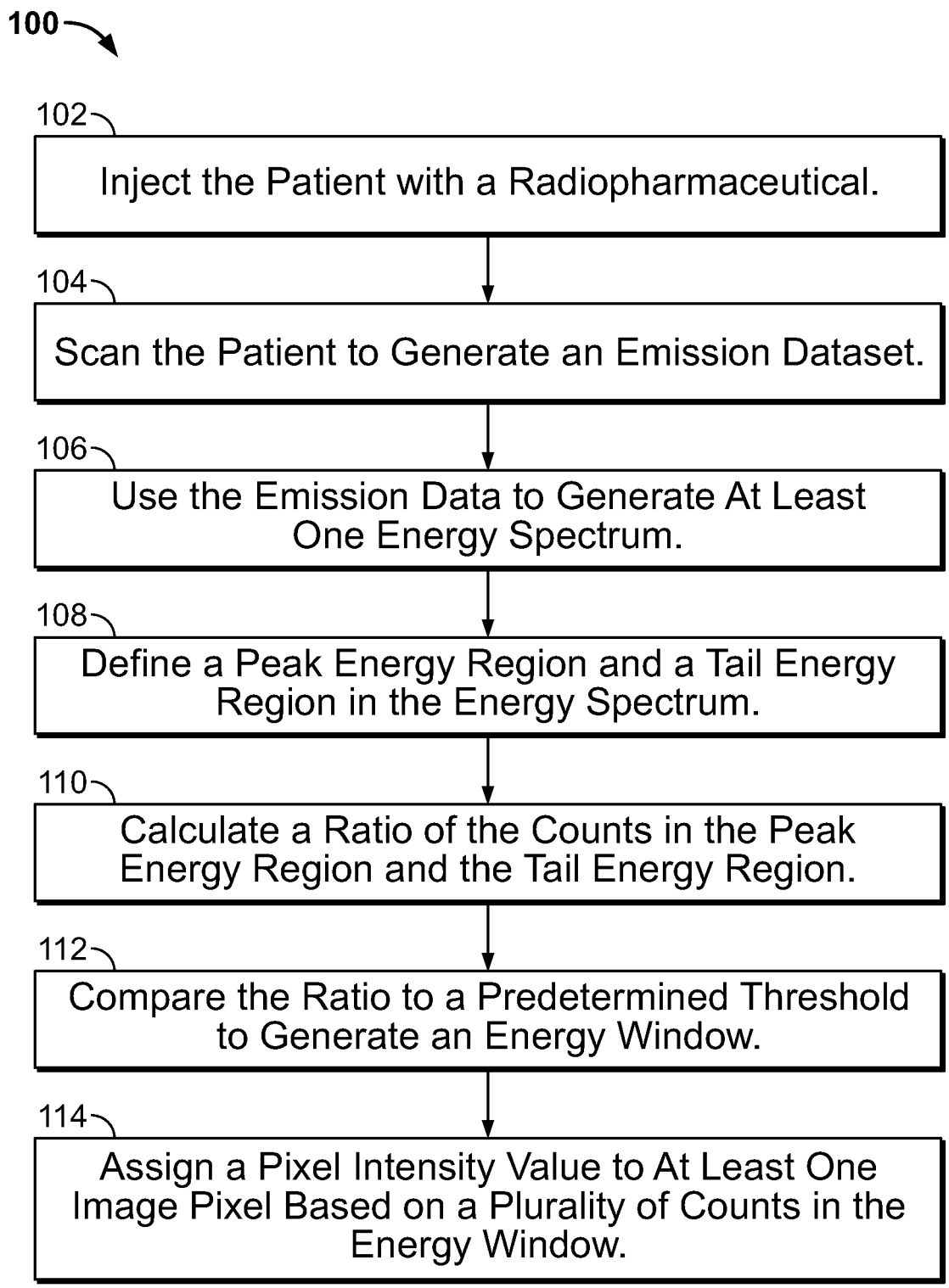
FIG. 2 is a method of automatically generate an energy window in accordance with various embodiments.

FIG. 2 is a simplified block diagram of an exemplary method 100 that may be utilized to automatically generate an energy window based on information obtained by analyzing the energy spectrums acquired from the detectors 12 and 14. As used herein, the energy window defines an energy range of the counts received by the detector elements 18. For example, for TC-99 specifically, the energy window may be initially configured to have a width that encompasses the counts centered on the peak energy of 140 keV. The method 100 further automatically adjusts the size of the energy window, and therefore the counts included within the energy window, based on an analysis of the scatter content in the energy spectrum. The counts within the energy window, after adjusting the size of the energy window, are then used to adjust a pixel intensity of various pixels in a final image. In the exemplary embodiment, the method 100 may be implemented using the processing unit 36 and/or the energy window generating module 60 (shown in FIG. 1). The method 100 may therefore be provided as a non-transitory computer-readable medium or media having instructions recorded thereon for directing the processing unit 36 and/or the motion detection and correction module 60 to perform an embodiment of the methods described herein. The medium or media may be any type of CD-ROM, DVD, floppy disk, hard disk, optical disk, flash RAM drive, or other type of computer-readable medium or a combination thereof.

Referring to FIG. 2, at 102 the patient is injected with a radiopharmaceutical. In the illustrated embodiment, the patient is injected with Technetium 99 (Tc-99) having a single energy peak of approximately 140 keV. However, it should be appreciated that the patient may be injected with any radiopharmaceutical, such as for example Cobalt or Barium, that is suitable for performing nuclear imaging, and Tc-99 is one such radiopharmaceutical.

Referring to FIG. 2, at 104 the patient's breast 20 is scanned to generate an emission dataset, such as the emission dataset 44 (shown in FIG. 1). The emission dataset 44 may be acquired using the MBI system 10 (shown in FIG. 1). For example, the emission dataset 44 may be acquired by performing a scan of the breast 20 to produce the emission dataset 44. Optionally, the emission dataset 44 may be acquired from data collected during a previous scan of the breast 20, wherein the emission dataset 44 has been stored in a memory, such as the data storage device 42 (shown in FIG. 1). The emission dataset 44 may be stored in any format, such as a plurality of 2D images 46 or a list mode dataset 48, for example. The emission dataset 44 may be acquired during real-time scanning of the breast 20. For example, the methods described herein may be performed on emission data as the emission dataset 44 is received from the MBI system 10 during a real-time examination of the breast 20.

In operation, the patient is initially injected with the radiopharmaceutical that emits gamma rays as the radiopharmaceutical decays. The emitted gamma rays have energy of for example, 140.5 keV for Tc-99. The gamma photons are detected by the detectors 12 and 14.

The number of gamma rays per unit time detected within a field of view (FOV) of the detectors 12 and 14 is the count rate of the detector. The count rate of the detector 12 or 14 are generally referred to as singles counts, or merely counts. Scatter coincidence events may occur because some gamma rays are deflected from their original direction due to interaction with a body part before reaching the detectors 12 and 14. Therefore, it is generally desirable to reject the scatter events during the acquisition of the emission dataset 44, because the images generated using only the events or counts represent a true activity distribution of radio-activity in the scanned body part of the patient. Moreover, scattered radiations may increase the background to the image, thus degrading the image contrast.

Figure 3:
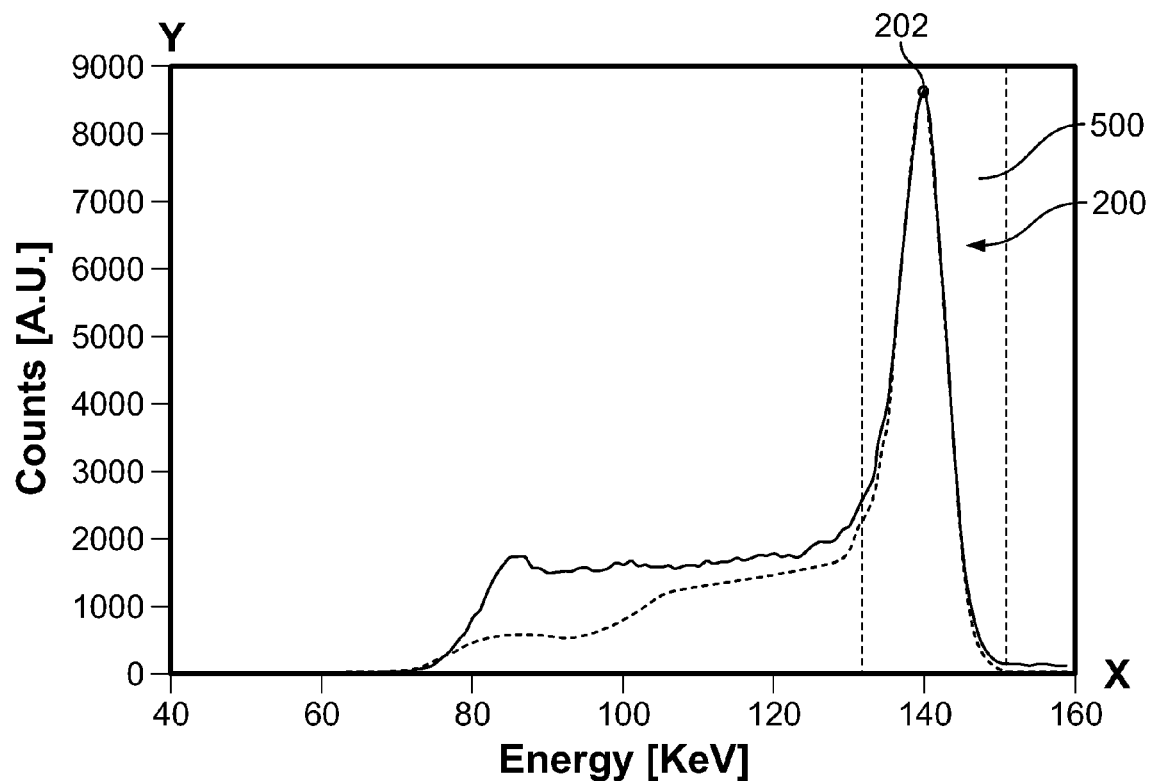
FIG. 3 is a graphical illustration of an energy spectrum that may be generated in accordance with various embodiments.

At 106, the emission data 44 is used to generate at least one energy spectrum. Energy spectrum as used herein is information that includes both the energy of the counts received by at least one the pixels in the detectors 12 and 14 and also the quantity of counts received by the at least one pixel in the detectors 12 and 14. For example, FIG. 3 is a graphical illustration of an exemplary energy spectrum 200 that may be generated using the emission dataset 44 wherein the X-axis represents the energy of the counts and the Y-axis represents the quantity of counts. In the illustrated embodiment, the energy spectrum 200 is generated using emission data acquired from a single detector element 18 in the detector 12. Optionally, the energy spectrum 200 may be generated using information acquired from a plurality of detector elements 18 as is described in more detail below.

In the illustrated embodiment, the energy spectrum 200 has a peak energy, denoted by point 202, of approximately 140 keV. More specifically, and in the exemplary embodiment, at 102 the patient is injected with Tc-99which has a peak energy of approximately 140 keV meaning that the majority of counts recorded by the detector 12 should be located proximate to the peak energy point 202 of Tc99, e.g. approximately 140 keV.

Figure 4:
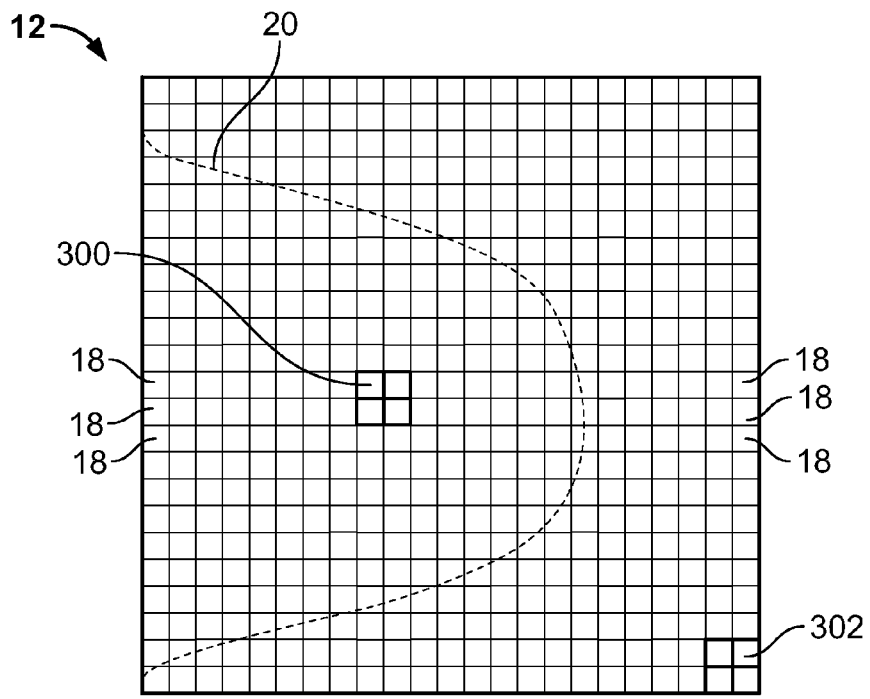
FIG. 4 is a front view of a pixilated detector formed in accordance with various embodiments.

In various embodiments, the energy spectrum 200 includes counts acquired from at least one detector element 18 and may include counts acquired from a plurality of detector elements 18. For example, FIG. 4 is a front view of the detector 12. Although the energy spectrums are described with respect to detector 12 it should be realized that similar energy spectrums may be acquired using information from the detector 14. As described above the detectors 12 and 14 are fabricated using CZT to form a pixilated detector that includes a plurality of detector elements 18. In operation, when the breast 20 is positioned between the detectors 12 and 14, the detector elements 18 nearest the breast 20 should record more counts than detector elements located away from the breast 20. For example, and as shown in FIG. 4, detector elements 300, are nearer to the gamma photons being emitted by the Tc-99 in the breast 20, the detector elements 300 should in general register a relatively high quantity of counts. Moreover, because detector elements 302 are farther from the gamma photons being emitted by the Tc-99 in the breast 20, the detector elements 302 should in general register a relatively lower quantity of counts than the detector elements 300. Accordingly, in various embodiments, an energy spectrum 200 is generated for each of the detector elements 300. Moreover, and in some embodiments, the information or counts generated by the detector elements 302 are combined to form a single energy spectrum. Therefore, a single energy spectrum may be generated for each of the detector elements 300 located nearer the center of the detector 12, and a single energy spectrum may be generated by combining counts recorded from a plurality of detector elements 302 located near the edge of the detector 12. Thus, the energy spectrum range (limits) 200 may derived from counts recorded by a single detector element 18 or a group of detector elements 18. It should be realized that in various embodiments, more than one pixel (range of pixels) may be used to determine the limits of the spectrum—energy range. The counts in each pixel in the image are the counts of this pixel counts only, in the energy range determined above.

Figure 5:
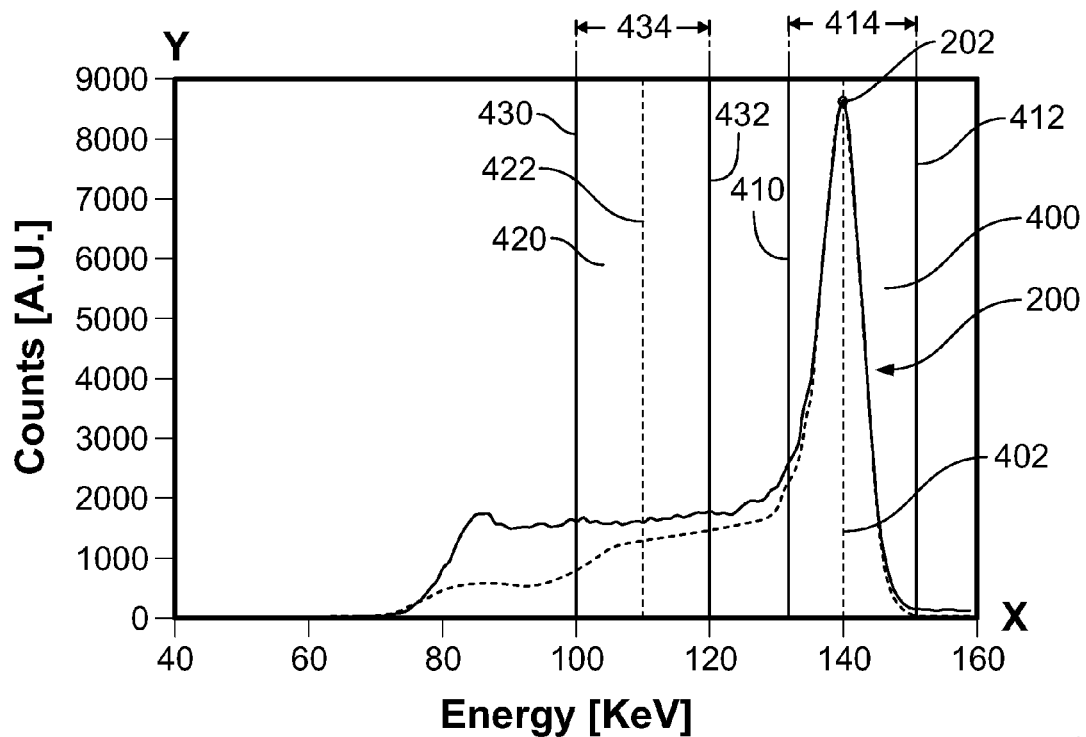
FIG. 5 is a graphical illustration of a peak energy region and tail energy region that may be generated in accordance with various embodiments.

Referring again to FIG. 2, at 108 a peak energy region and a tail energy region in the energy spectrum 200 are determined. It should be realized that although determining a peak energy region and a tail energy region are discussed with respect to the exemplary energy spectrum 200, that a peak energy region and tail energy region are determined for each of the energy spectrums generated at 106. As used herein, the term peak energy region means a bin or window that encapsulates the portion of the energy spectrum 200 that defines counts having a range of energy levels including, but not necessarily exactly symmetric around the peak, the energy of the radioisotope administered at 102. Accordingly, in the exemplary embodiment, and as shown in FIG. 5, a peak energy region 400 of the energy spectrum 200 has a center 402 proximate to the peak energy 202 of Tc-99, e.g. 140 kev.

In the illustrated embodiment, the peak energy region 400 has a first side 410 and a second side 412 that define a width 414 of the peak energy region 400. As described above the center 402 of the peak energy region 400 is located proximate to the peak energy 202 of the radioisotope. The initial width 414 of the peak energy region 400 may be determined based on apriori information of the operational physics of the detector 12 and/or the physical characteristics of the portion of the patient being imaged. In the illustrated embodiment, the width 414 of the peak energy region 400 is set to approximately ±10% percent of the peak energy of Tc-99, e.g. ±10% of 140 keV, such that the initial width 414 of the peak energy region 400 extends from approximately 126 keV to approximately 154 keV in the illustrated embodiment.

At 108, a tail energy region in the energy spectrum 200 is also determined. As used herein, the term tail energy region means a window or portion of the energy spectrum 200 that defines counts having a range of energy levels that are not included within the peak energy region 400. Accordingly, in the exemplary embodiment, and as shown in FIG. 5, a tail energy region 420 may be defined to have a center 422 around, for example, 110 keV.

In the illustrated embodiment, the tail energy region 420 has a first side 430 and a second side 432 that define a width 434 of the tail energy region 400. The initial width 434 of the tail energy region 420 may also be determined based on apriori information of the operational physics of the detector 12 and/or the physical characteristics of the portion of the patient being imaged. In the illustrated embodiment, the width 434 of the tail energy region 420 is set to approximately ±10% percent of 110 keV, such that the initial width 434 of the tail energy region 420 extends from approximately 99 keV to approximately 121 keV in the illustrated embodiment.

At 110, a ratio of the counts in the peak energy region 400 and the counts in the tail energy region 420 are calculated in accordance with:

$$\text{Ratio} = \frac{\int_{430}^{432} \text{counts}}{\int_{410}^{412} \text{counts}}; \quad \text{Equation 1}$$

wherein, and as described above, 410 and 412 set the low and high energy ranges of the peak energy region 400, and 430 and 432 set the low and high energy ranges of the tail energy region 420. Thus, the ratio represents a comparison of the counts in the peak energy region 400 and the counts in the tail energy region 420. It should be realized that while the illustrated embodiment describes generating the ratio by comparing the counts in two windows, e.g. the peak energy region 400 and the tail energy region 420, that more than two energy regions may be defined in the energy spectrum 200 and therefore the ratio may be determined using the counts in the more than two energy regions.

Figure 6:
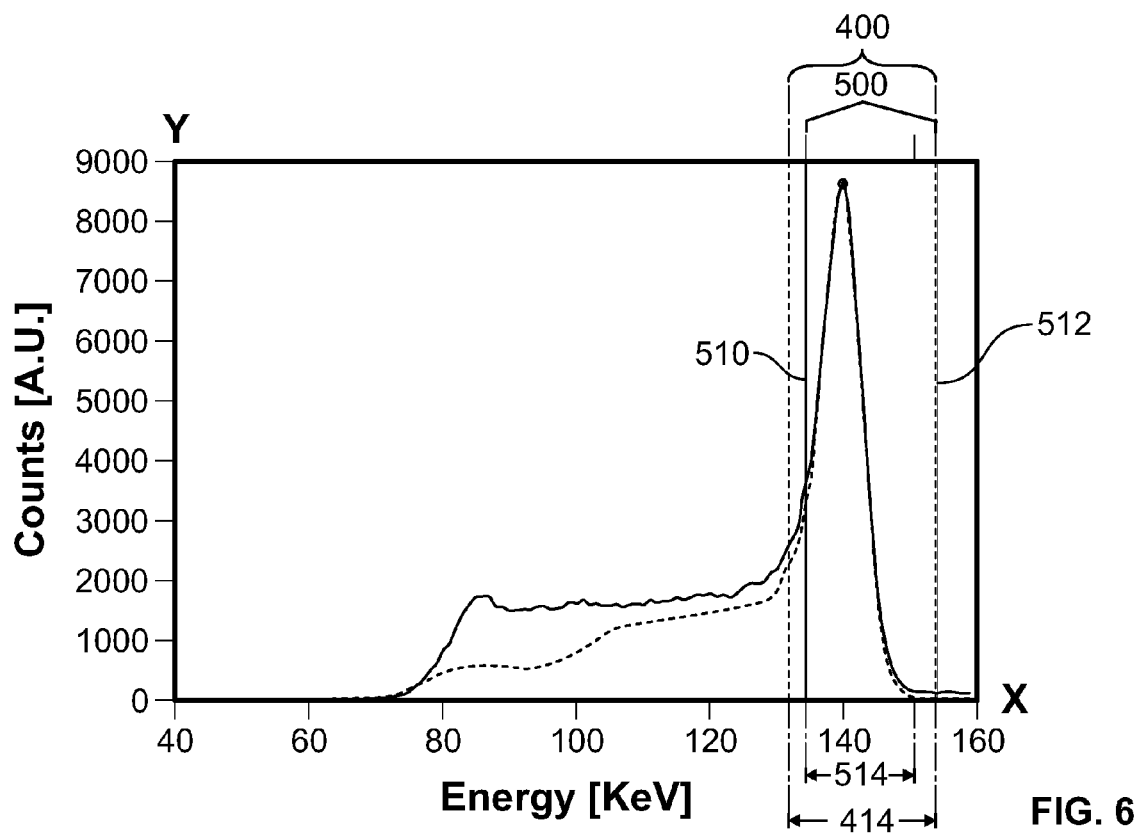
FIG. 6 is a graphical illustration of an energy window that may be generated in accordance with various embodiments.

At 112, the ratio calculated at 110 is compared to a predetermined scatter threshold to generate an energy window, such as the energy window 500 shown in FIG. 6. The energy window 500 has first side 510 and a second side 512 that define the lower and upper energy ranges of the energy window 500. Moreover, the energy window 500 has a width 514 that is defined between the first side 510 and the second side 512. The counts within the energy window 500 are utilized to determine a pixel intensity value of the detector element or elements that were used to generate the energy spectrum 200.

In operation, the predetermined scatter threshold is utilized to quantify the amount of scatter in the energy spectrum 200. The predetermined threshold may be set automatically by the processing unit 36 to a value of, for example, 0.6. Optionally, the predetermined threshold may be entered manually by the user utilizing the input device 50.

In one embodiment, if Count Ratio>Predetermined scatter threshold, this indicates that the scatter is significant in the region wherein the detector element 118 is located in the detector 12. For example, the detector element 118 may be located proximate to the chest wall of the patient being imaged. Accordingly, to facilitate reducing scatter in a final image, the width 514 of the energy window 500 is reduced, compared to the width 414 of the peak energy region 400, to facilitate reducing counts that may occur because of scatter. In the illustrated, the width 514 of the energy window 500 may be set to include counts having from approximately 138 keV to approximately 147 keV, e.g. the width 514 is approximately ±5% of the peak energy 140 keV.

It should be realized that while the illustrated embodiment shows the center of the energy window 500 be located at the peak energy 202 and the first and second sides 510 and 512 being offset from the peak energy by 5%, that the energy window 500 may in some embodiments be offset from the peak energy 212. For example, while the energy window 500 may have a reduced width of approximately 5% of the peak energy 212, the left side 510 of the energy window 500 may be located, for example at 132 keV and the right side 512 of the energy window 500 may be located at, for example 147 keV (the left side is not effected by scatter and therefore may kept constant). In some embodiments, the right side of the energy window 500 may be located at the same position as the right side of the peak energy region 400. Accordingly, the width 514 of the energy window 500 may be reduced to include less counts, and therefore less counts attributable to scatter, for regions of the detector 12 that are located near the chest wall such that scatter from the liver, heart, etc. may affect the quality of the final image.

Figure 7:
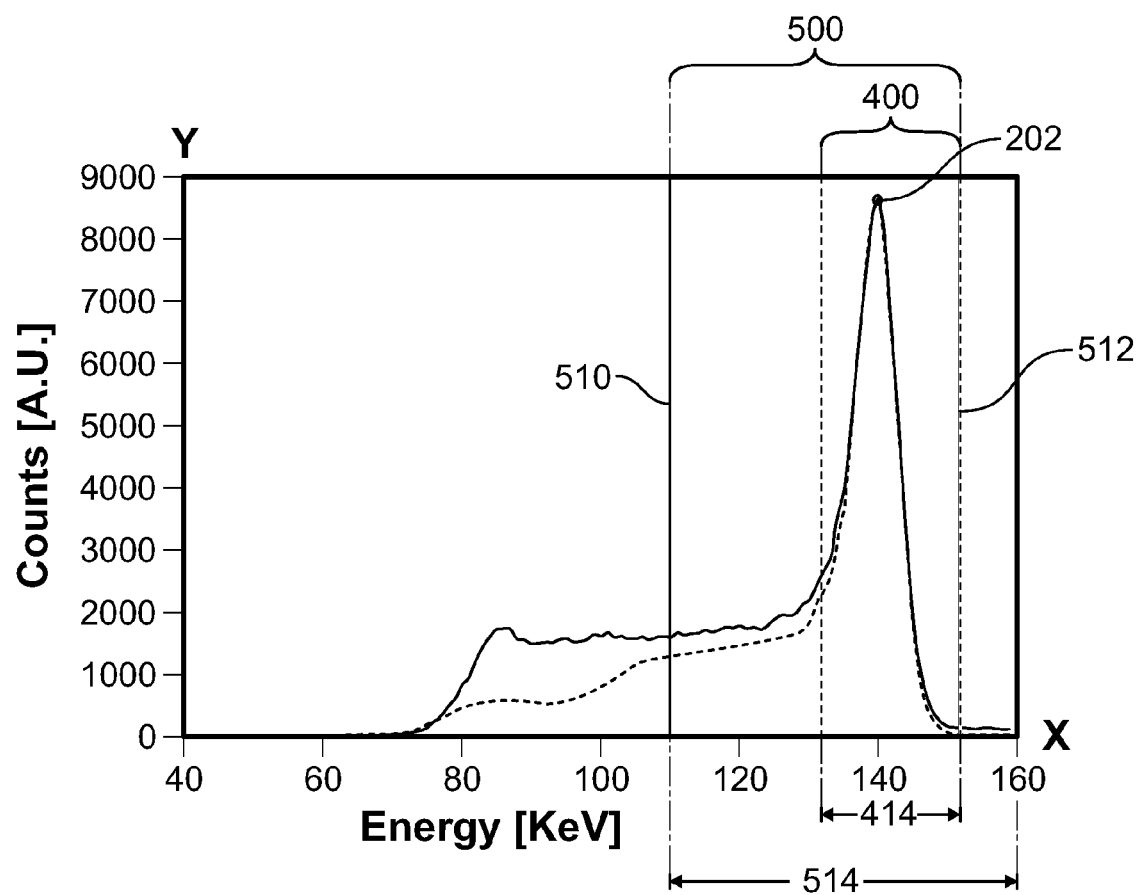
FIG. 7 is a graphical illustration of another energy window that may be generated in accordance with various embodiments.

In another embodiment, the Count Ratio <Predetermined scatter threshold which indicates that the scatter is not significant in the region wherein the detector element 118 is located in the detector 12. For example, the detector element 118 may be located away from the chest wall of the patient being imaged. Accordingly, because the scatter counts are relatively low in this region of the detector 12, the width 514 of the energy window 500 is increased as shown in FIG. 7, compared to the width 414 of the peak energy region 400, to facilitate increasing the counts used to generate the final image. In the illustrated, the width 514 of the energy window 500 may be set to include counts having from approximately 125 keV to approximately 155 keV or 147, e.g. the width 514 is approximately ±10% or [−10%+5%] of the peak energy 140 keV.

It should be realized that while the illustrated embodiment shows the center of the energy window 500 be located at the peak energy 202 and the first and second sides 510 and 512 being offset from the peak energy by 10%, that the energy window 500 may in some embodiments be offset from the peak energy 212. For example, while the energy window 500 may have an increased width of approximately 10% of the peak energy 212, the left side 510 of the energy window 500 may be located, for example at 120 keV and the right side 512 of the energy window 500 may be located at, for example 150 keV. Accordingly, the width 514 of the energy window 500 may be increased to include more counts for regions of the detector 12 that are located away from the chest wall where scatter from the liver, heart, etc. do not affect the quality of the final image.

Referring again to FIG. 2, at 114 a pixel intensity value is assigned to the detector element 18 based on a plurality of counts in the energy window 500.

In the exemplary embodiment, steps 106-114 are iteratively repeated for each detector element 18, or group of detector elements, in the detector 12 until each of the detector elements 18 is assigned an intensity value. An image of the breast 20 may then be generated using the pixel intensity values assigned at 114. The intensity value of each pixel may be corrected using calibrating factor specific to the energy window used.

Described herein are methods and systems for identifying scatter related counts in an emission dataset. As described above, a CZT energy spectrum includes a peak energy region and a tail region. The ratio of counts between the peak energy region and the tail energy region may therefore be utilized to quantify the amount of scatter in the emission dataset 44. The quantified scatter is then used to generate an energy window. A wider energy window may improve the diagnostic quality of a final image wherein scatter counts are relatively low. Moreover, a narrower energy window may improve lesion detectability in regions that are affected by scatter by reducing and/or eliminating counts that may occur as scatter related events in the final image.

A width of an energy window may therefore be increased to include more counts when the scatter counts are relatively low or decreased when the scatter counts are relatively high. The counts within the energy window are then used to generate an image. The methods described herein may be performed automatically using the processing unit 36 or the energy window generating module 60. Optionally, a portion of the method may be performed manually by a user. For example, a user may manually select, using the input device 50, one or more detector elements 18 to combine to generate the energy spectrum 200. The user may manually select the locations of the peak energy region 400 and/or the tail energy region 420. The user may manually resize the peak energy region 400 and/or the tail energy region 420 after being initially generated by the processing unit 36. Moreover, the user may manually resize the energy window 500 after being initially generated by the processing unit 36.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for generating molecular breast imaging (MBI) images, said method comprising:
    generating at least one energy spectrum using an emission dataset acquired by imaging a patient,
    identifying a tail energy region and a peak energy region in the energy spectrum;
    determining a quantity of counts in the tail energy region and the peak energy region;
    generating an energy window for the energy spectrum based on the counts in the tail energy region and the peak energy region; and
    assigning a pixel intensity value to at least one image pixel based on a plurality of counts in the energy window.

2. The method of claim 1, further comprising:
    generating a ratio of the counts in the tail energy region and the counts in the peak energy region; and
    generating the energy window based on the ratio.

3. The method of claim 1, further comprising:
    generating a ratio of the counts in the tail energy region and the counts in the peak energy region;
    decreasing a width of the energy window when the ratio is greater than a predetermined threshold; and
    increasing a width of the energy window when the ratio is less than the predetermined threshold.

4. The method of claim 1, further comprising:
    generating a plurality of energy spectrums using the emission dataset; and
    generating an energy window for each of the energy spectrums; and
    assigning a pixel intensity value to a plurality of image pixels using the counts in the energy windows.

5. The method of claim 1, further comprising:
    generating a ratio of the counts in the tail energy region and the counts in the peak energy region; and
    comparing the ratio to a predetermined threshold to generate the energy window.

6. The method of claim 5, further comprising:
    increasing a width of the energy window when the ratio is less than the predetermined threshold; and
    decreasing the width of the energy window when the ratio is greater than the predetermined threshold.

7. The method of claim 5, wherein the predetermined threshold is 0.6.

8. The method of claim 1, further comprising generating the emission dataset using a molecular breast imaging (MBI) system.

9. The method of claim 1, further comprising generating the least one energy spectrum using an emission dataset acquired by imaging a breast.

10. A molecular breast imaging (MBI) system comprising:
at least one detector having a plurality of detector elements; and
a processing unit coupled to the detector, the processing unit configured to
generate at least one energy spectrum using an emission dataset acquired by imaging a patient,
identify a tail energy region and a peak energy region in the energy spectrum;
determine a quantity of counts in the tail energy region and the peak energy region;
generate an energy window for the energy spectrum based on the counts in the tail energy region and the peak energy region; and
assign a pixel intensity value to at least one image pixel based on a plurality of counts in the energy window.

11. The MBI system of claim 10, wherein the at least one detector comprises a pair of CZT detectors configured to generate the emission dataset.

12. The MBI system of claim 10, wherein the processing unit is further configured to:
generate a ratio of the counts in the tail energy region and the counts in the peak energy region; and
generate the energy window based on the ratio.

13. The MBI system of claim 10, wherein the processing unit is further configured to:
generate a ratio of the counts in the tail energy region and the counts in the peak energy region;
automatically decrease a width of the energy window when the ratio is greater than a predetermined threshold; and
automatically increase a width of the energy window when the ratio is less than the predetermined threshold.

14. The MBI system of claim 10, wherein the processing unit is further configured to:
generate a plurality of energy spectrums using the emission dataset; and
generate an energy window for each of the energy spectrums; and
assign a pixel intensity value to a plurality of image pixels using the counts in the energy windows.

15. The MBI system of claim 10, wherein the processing unit is further configured to:
generate a ratio of the counts in the tail energy region and the counts in the peak energy region; and
compare the ratio to a predetermined threshold to generate the energy window.

16. The MBI system of claim 15, wherein the processing unit is further configured to:
increase a width of the energy window when the ratio is less than a predetermined threshold; and
decrease the width of the energy window when the ratio is greater than the predetermined threshold.

17. A non-transitory computer readable medium encoded with a program to instruct a processing unit to:
generate at least one energy spectrum using an emission dataset acquired by imaging a patient,
identify a tail energy region and a peak energy region in the energy spectrum;
determine a quantity of counts in the tail energy region and the peak energy region;
generate an energy window for the energy spectrum based on the counts in the tail energy region and the peak energy region; and
assign a pixel intensity value to at least one image pixel based on a plurality of counts in the energy window.

18. The non-transitory computer readable medium of claim 17, further encoded with a program to instruct the processing unit to:
generate a ratio of the counts in the tail energy region and the counts in the peak energy region; and
generate the energy window based on the ratio.

19. The non-transitory computer readable medium of claim 17, further encoded with a program to instruct the processing unit to:
generate a ratio of the counts in the tail energy region and the counts in the peak energy region;
automatically decrease a width of the energy window when the ratio is greater than a predetermined threshold; and
automatically increase a width of the energy window when the ratio is less than the predetermined threshold.

20. The non-transitory computer readable medium of claim 17, further encoded with a program to instruct the processing unit to:
generate a ratio of the counts in the tail energy region and the counts in the peak energy region; and
compare the ratio to a predetermined threshold to generate the energy window.

\* \* \* \* \*